US00PP25662P2

(12) United States Plant Patent
Lannes

(10) Patent No.: US PP25,662 P2
(45) Date of Patent: Jun. 30, 2015

(54) ***HIBISCUS* PLANT NAMED 'LANSABINE'**

(50) Latin Name: *Hibiscus rosa-sinensis*
Varietal Denomination: Lansabine

(71) Applicant: Robert Lannes, Malause (FR)

(72) Inventor: Robert Lannes, Malause (FR)

( * ) Notice: Subject to any disclaimer, the term of this patent is extended or adjusted under 35 U.S.C. 154(b) by 177 days.

(21) Appl. No.: 13/987,547

(22) Filed: Aug. 6, 2013

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — June Hwu
(74) *Attorney, Agent, or Firm* — Penny J. Aguirre

(57) ABSTRACT

A new cultivar of *Hibiscus* named 'Lansabine', characterized by its large flowers that are round in shape and "chiffon" pink in color, its short leaf internode lengths, its very dark green foliage, and its good self-branching habit.

2 Drawing Sheets

Botanical classification: *Hibiscus rosa-sinensis*.
Cultivar designation: 'Lansabine'.

BACKGROUND OF THE INVENTION

The present invention relates to a new and distinct cultivar of *Hibiscus* plant of hybrid origin, botanically known as *Hibiscus rosa-sinensis* 'Lansabine' and will be referred to hereafter by its cultivar name, 'Lansabine'. 'Lansabine' is a new cultivar of tropical *Hibiscus* grown for use as a landscape and container plant.

The new cultivar was developed through an on-going breeding program conducted by the Inventor in Malause, France. The objectives of the breeding program are to develop new cultivars of *Hibiscus* that exhibit compact plant habits with self-branching and a well-balanced plant habit.

The Inventor made a cross in July of 2005 between 'Nelly Rose Clair' (not patented) as the female parent and 'Mercedes' (not patented) as the male parent. 'Lansabine' was selected as a single unique plant from the resulting seedlings in September of 2009.

Asexual propagation of the new cultivar was first accomplished by stem cuttings in Malause, France in September of 2009 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics 'Lansabine'. These attributes in combination distinguish 'Lansabine' as a new and distinct cultivar of *Hibiscus*.

1. 'Lansabine' exhibits large flowers that are round in shape and "chiffon" pink in color.
2. 'Lansabine' exhibits short leaf internode lengths.
3. 'Lansabine' exhibits very dark green foliage.
4. 'Lansabine' exhibits good self-branching.

Both the female parent of 'Lansabine', 'Nelly Rose Clair', and the male parent, 'Mercedes', differ from 'Lansabine' in having flowers that are darker pink in color, in having a more vigorous growth habit, and in having longer stems with less self-branching. 'Lansabine' can also be most closely compared to the cultivars 'Bellona' (not patented) and 'Cancun' (not patented). Both are similar to 'Lansabine' in having flowers that are pink in color. 'Bellona' differs from 'Lansabine' in having flowers that are darker pink in color with a black eye zone and in having stems with less self-branching and longer leaf internodes. 'Cancun' differs from 'Lansabine' in having smaller flowers with a red eye zone.

BRIEF DESCRIPTION OF THE DRAWING

The accompanying colored photograph illustrates the overall appearance and distinct characteristics of the new *Hibiscus*. The photographs were taken of a six month-old plant of 'Lansabine' as grown in a one-gallon container in a greenhouse in Malause, France.

The photograph in FIG. 1 provides a side view of 'Lansabine' in bloom.

Figure 1:
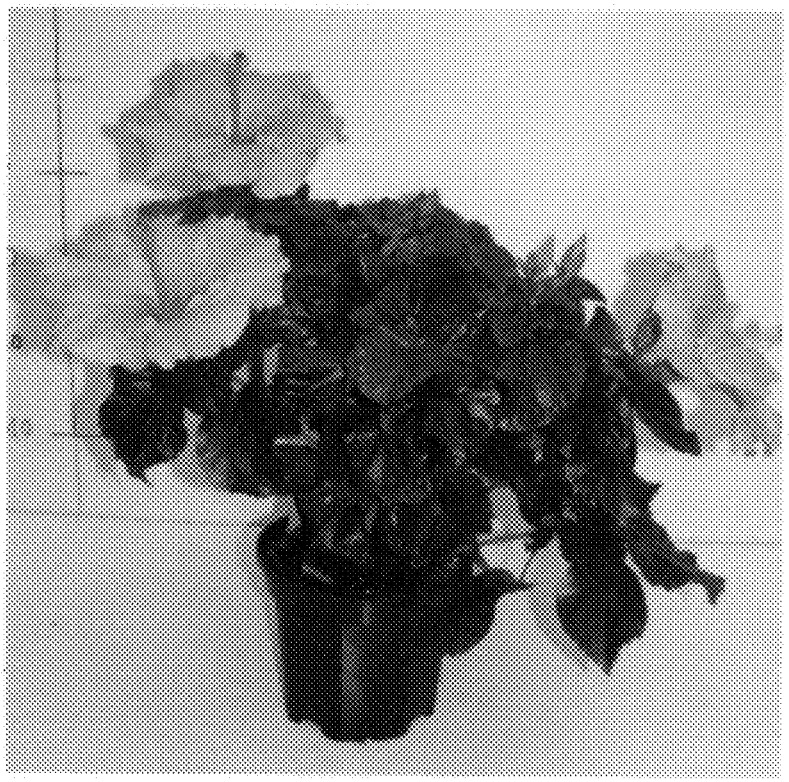
Figure 2:
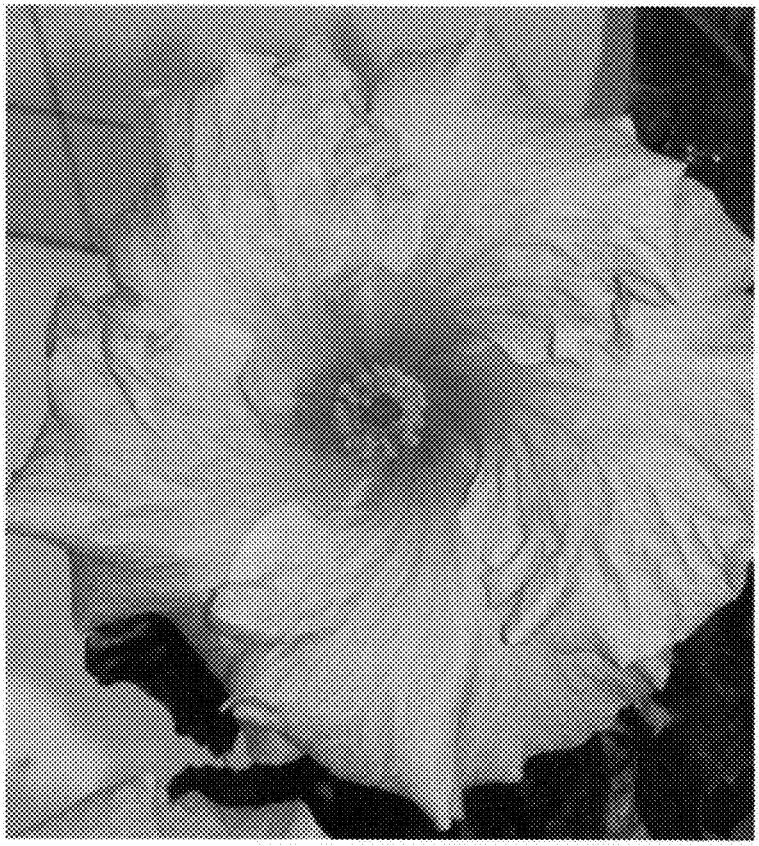

The photograph in FIG. 2 provides a close-up view of a flower of 'Lansabine'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 8 month-old plants of the new cultivar as grown in two-quart containers in a greenhouse in Grand Saline, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—Continuously through summer in Grand Saline, Tex. and Malause, France.

*Plant type*.—Tropical evergreen shrub.
*Plant habit*.—Upright and slightly spreading, compact.
*Height and spread*.—Reaches 40 to 50 cm in height and 30 to 35 cm in spread.
*Hardiness*.—At least in U.S.D.A. Zones 9 to 11.
*Diseases*.—Not susceptible or resistance to diseases has been observed.
*Root description*.—Fibrous roots.
*Propagation*.—Stem cutting.
*Growth rate*.—Moderate.

Stem description:
*Shape*.—Slightly oval.
*Stem color*.—New growth; 138A with overlay of 199A in some areas, mature wood; 156B with striations of 165C.
*Stem size*.—Main stems; an average of 20 cm in length and 5 mm in width, lateral stems; an average of 15 cm in length and 4 mm in diameter.
*Stem surface*.—New growth; pubescent, bark; finely striated.
*Stem aspect*.—Held upright to an average angle of 35° (0°=vertical).
*Stem strength*.—Strong.
*Branching*.—Self-branching, an average of 2 main stems and 2 lateral branches per main stem in a gallon container.
*Internode*.—Average of 2.9 cm.

Foliage description:
*Leaf shape*.—Ovate.
*Leaf division*.—Simple.
*Leaf base*.—Rounded.
*Leaf apex*.—Acute.
*Leaf venation*.—Pinnate, 138A in color on upper and lower surface.
*Leaf margins*.—Crenate.
*Leaf attachment*.—Petiolate.
*Leaf arrangement*.—Alternate.
*Leaf orientation*.—Held horizontal.
*Leaf aspect*.—Slightly cupped upward.
*Leaf surface*.—Upper surface sparsely pubescent and glossy, lower surface sparsely pubescent along the veins and satiny.
*Leaf color*.—Young leaves upper surface 137A; young leaves lower surface 138A; mature leaves upper surface; 135A; mature leaves lower surface; 138A.
*Leaf size*.—Average of 10.2 cm in length, and 7.6 cm in width.
*Leaf quantity*.—About 6 leaves per lateral branch 20 cm in length.
*Petioles*.—Average of 3.5 cm in length and 2 mm in diameter, 138A with overlay of 199A in some places, pubescent surface.

Flower description:
*Inflorescence type*.—Flowers are solitary.
*Lastingness of flowers*.—About 1 day, self cleaning.
*Flower size*.—An average of 6 cm in depth (including reproductive organs, without 4 cm) and 10 cm in diameter.
*Flower fragrance*.—None.
*Flower shape*.—Rotate.
*Flower number*.—Average of 2 per lateral stem at one time, continuously produces throughout the summer.
*Flower aspect*.—Outward to slightly reflexed.
*Flower bud*.—Elliptic in shape, an average of 4 cm in length and 2 cm in width, color sepal portion; a blend of 61C and 4B, base is 68B.
*Flower attachment*.—Peduncle.
*Petal number*.—5.
*Petal shape*.—Obcordate.
*Petal color*.—Upper surface when opening and fully opened; 67D with small eye zone 67B, lower surface when opening and fully opened; 65A, with outer edges mixing with 4B.
*Petal surface*.—Both surfaces smooth dull on upper portion and satiny near base.
*Petal margins*.—Very slightly crenated and slightly wavy.
*Petal apex*.—Rounded.
*Petal base*.—Slightly oblique and adnate to base of style.
*Petal size*.—Average of 6 cm in length and 6 cm in width.
*Sepal number*.—5.
*Sepal shape*.—Elliptic.
*Sepal margin*.—Entire.
*Sepal size*.—Average of 3 cm in length and 1 cm in width.
*Sepal aspect*.—Upright, lower 50% fused.
*Sepal surface*.—Upper surface pubescent, lower surface smooth and glossy.
*Sepal apex*.—Acute-slightly acuminate.
*Sepal base*.—Fused.
*Sepal color*.—Young and mature upper (outer) and lower (inner) surface; a blend of 150C and 143A.
*Calyx*.—Campanulate in shape, average of 3 cm in length and 3 cm in diameter.
*Peduncles*.—An average of 4 cm in length and 3 mm in diameter, strong, average angle is 45° and 144A in color, finely pubescent surface.
*Pedicels*.—Not present, flowers are solitary from terminal leaf axils.
*Bracts*.—Average of 8 bracts held upright surrounding sepals, lanceolate-linear in shape, narrowly acute apex, truncate base, average of 1 cm in length and 3 mm in width, upper and lower surface N137A base 144B, both surfaces are smooth.

Reproductive organs:
*Gynoecium*.—1 pistil, about 6.5 cm in length, stigmas; an average of 5, and 187D in color, style; 5 cm in length and color is 63D at the top and mid section blending into 58C at mid section to base, ovary; 1 cm in length and width, 69D in color and is completely covered by the base of the pistil style.
*Androecium*.—Stamens; average of 50, stamens are clustered and implanted into upper portion of style, anthers; dorsifixed and orbicular in shape, 2 mm in diameter, and 16A in color; filament; 2 mm in length, 0.2 mm in width, and 58C in color, pollen; abundant in quantity and 16A in color.
*Fruit/seeds*.—None observed.

It is claimed:

1. A new and distinct cultivar of *Hibiscus* plant named 'Lansabine' as herein illustrated and described.

* * * * *